United States Patent [19]

Hu et al.

[11] Patent Number: 4,496,479

[45] Date of Patent: Jan. 29, 1985

[54] CHLORAMPHENICOL DERIVATIVES, ANTIGENS AND ANTIBODIES

[75] Inventors: Mae W. Hu; Prithipal Singh, both of Sunnyvale, Calif.

[73] Assignee: Syntex (U.S.A.) Company, Palo Alto, Calif.

[21] Appl. No.: 495,851

[22] Filed: May 18, 1983

[51] Int. Cl.³ .............................................. A61K 31/04
[52] U.S. Cl. ............................ 260/112 R; 260/112 B; 260/121; 560/43; 564/212; 564/213; 435/177
[58] Field of Search ........ 260/112 R, 112 B, 112.5 R, 260/121; 424/1, 177, 188, 805, 810; 564/212, 213; 560/43

[56] References Cited

U.S. PATENT DOCUMENTS

| 2,483,884 | 10/1949 | Crooks, Jr. et al. | 564/213 |
| 2,483,885 | 10/1949 | Crooks, Jr. et al. | 260/465 D |
| 4,177,038 | 12/1979 | Biebricher et al. | 435/178 |

Primary Examiner—John Kight
Assistant Examiner—Nathan M. Nutter
Attorney, Agent, or Firm—Theodore J. Leitereg

[57] ABSTRACT

Chloramphenicol derivatives are provided for use in preparing antigen conjugates for the production of antibodies specific for chloramphenicol. Specifically, the aryl group is derivatized with a side chain functionalized to provide for a carbonyl functionality to react with amino groups of a poly(amino acid). The conjugate is then injected into a vertebrate for production of antisera which are isolated in conventional ways and find particular use in competitive protein binding assays.

15 Claims, No Drawings

CHLORAMPHENICOL DERIVATIVES, ANTIGENS AND ANTIBODIES

BACKGROUND OF THE INVENTION

1. Field of the Invention

In performing immunoassays, it is necessary to have a receptor which specifically recognizes the compound or compounds of interest while having weak or no binding to compounds of similar structure which may be encountered in the samples of interest. In order to obtain antisera, when haptens are involved, it is necessary that derivatives of the hapten be designed for conjugation to an antigen, where the resulting antisera will provide for the desired specificity. In many situations, the hapten of interest is highly functionalized, so that the synthetic procedure for the derivative must be designed to maintain the integrity of the structural features of the haptens.

2. Description of the Prior Art

U.S. Pat. No. 3,817,837 describes an enzyme immunoassay. Hamburger and Douglass, *Immunology*, 1969, 17(4) 599–602; Orgel and Hamburger, ibid, 1971, 20(2), 233–9; Hamburger and Douglass, ibid, 1969, 17(4), 58791 and Hamburger, *Science* 152 (379), 203–5 (1966) describe various antibodies to chloramphenicol. Copending applications Ser. No. 256,761, filed Apr. 23, 1981, and Ser. No. 306,569, filed Sept. 28, 1981, are concerned with chloramphenicol derivatives, antigens, and antibodies. Analogs of chloramphenicol, namely, 2-dichloroacetamido-1-(4-chloro-3-nitrophenyl)propane-1,3-diol and 2-dichloroacetamido-1-(4-bromo-3-nitrophenyl)propane-1,3-diol, are discussed in CA: 88(5)37348n and CA: 74(23)125087t.

SUMMARY OF THE INVENTION

Chloramphenicol derivatives are prepared for conjugation to poly(amino acids) to prepare antigens for the production of antibodies and enzyme conjugates, where the enzyme conjugates and antibodies are used in combination for the determination of chloramphenicol. Particularly, the benzene group of chloramphenicol is derivatized with a side chain which contains a carbonyl functionality to react with amino groups of poly(amino acids). The carbonyl functionality may be an oxocarbonyl (carbonyl group), which would form a single bond, by reductive amination, with available amino groups of a poly(amino acid), or a non-oxo-carbonyl (substituted carbonyl group) such as an oxycarbonyl (carboxy), alkoxycarbonyl (ester), carboxycarbonyl (anhydride), or halocarbonyl (halide), which would form peptide bonds with a poly(amino acid). The conjugated antigens are employed in conventional ways for the production of antibodies specific for chloramphenicol.

DESCRIPTION OF THE SPECIFIC EMBODIMENTS

The subject invention is concerned with the preparation of reagents for use in diagnostic immunoassays for chloramphenicol. Specifically, the benzene group of chloramphenicol is derivatized with a side chain which contains a carbonyl functionality (including nitrogen-imino and sulfur analogs) for linking to available amino groups of a poly(amino acid). The carbonyl functionality will normally be separated from the benzene group by a bond or linking atom, e.g., chalcogen (oxygen or sulfur) or nitrogen, and a linking group of at least about 1 carbon atom and not more than about 12 atoms other than hydrogen, preferably 1 to 8 atoms, more preferably, 1 to 5 atoms. Where more than one atom is present in the linking group, the atoms may be carbon, nitrogen, chalcogen (oxygen and sulfur), usually carbon and chalcogen. There is normally not more than one heteroatom in the linking group. The heteroatom is generally bonded to carbon atoms, with chalcogen normally bonded to saturated carbon atoms where the heteratom is normally spaced two carbon atoms apart. When the carbonyl functionality is an oxo-carbonyl (aldehyde or ketone), a single bond will usually be formed by reductive amination with available amino groups of the poly(amino acid). When the carbonyl functionality is a non-oxo-carbonyl, peptide bonds will normally be formed. The oxycarbonyl (carboxy) can be activated in a variety of ways to react with amino groups to form peptide bonds.

For the preparation of antibodies, the chloramphenicol derivative will be conjugated to an antigenic poly(amino acid), which may then be injected into vertebrates, particularly domestic animals, for production of antibodies. After a repeated number of injections based on a predetermined schedule, the antibodies may be harvested from the serum and may be used as obtained or further purified so as to concentrate the antibodies of interest.

For the most part, the compounds of this invention will have the following formula:

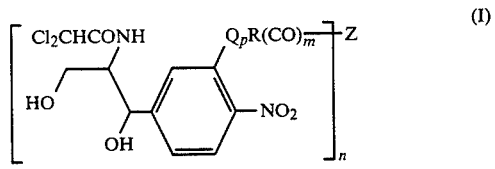

wherein:

Q is chalcogen of atomic number 8 to 16 (oxygen or sulfur) or nitrogen;

p is 0 or 1;

R is a linking group, usually aliphatic, of at least 1 carbon atom but not more than 12 atoms other than hydrogen, normally having from about 1 to 5 atoms in the chain, more preferably 1 to 3, wherein the atoms in the chain are normally carbon but, when several carbon atoms are present, may include not more than one heteroatom which may be nitrogen or chalcogen of atomic number 8 to 16 (oxygen or sulfur), wherein the heteroatom, if present, is bonded to other than hydrogen and chalcogen is bonded solely to saturated carbon atoms where the heteroatom is normally spaced two carbon atoms apart;

Z is hydrogen, hydroxy, alkoxy of from about 1 to 6 carbon atoms, more usually of 1 to 3 carbon atoms, an activating group capable of activating the carboxy group for forming peptide bonds in an aqueous medium with a poly(amino acid), e.g., p-nitrophenyl ester or N-oxy succinimide ester or Y, wherein Y is a poly(amino acid) residue, such as a polypeptide including proteins having 1 or more subunits, of at least about 2,000, more usually at least about 10,000 molecular weight and may be 10,000,000 or more molecular weight, usually not more than 1,000,000, functioning as either an antigen or enzyme;

m is 0 or 1, being 1 when Z is other than Y; and n is at least 1, when Z is other than Y, being 1 and when Z is Y, being a number between one and the molecular weight of Y divided by 1000, usually divided by 2,000, more usually divided by 3,000; when Y acts as an antigen, n is generally from about 1 to 100, usually 5 to 80; and when Y is an antigen of molecular weight of from about 30,000 to 300,000, n is generally from about 10 to 100; and when Y functions as an enzyme, n is from about 1 to 30, usually from about 2 to 20, more usually from about 2 to 16.

Preferred R groups include alkylene, e.g., methylene or polymethylene which are of particular interest, alkenylene, alkyleneoxyalkylene (wherein the heteroatom is separated from Q by at least 2 carbon atoms), N-lower alkyl (1–3 carbon atoms), alkyleneaminoalkylene (wherein the heteroatom is separated from Q by at least 2 carbon atoms).

The compounds of primary interest are those where Z is Y and find use as antigens or enzyme conjugates, Y being a poly(amino acid), functioning as either an antigen or an enzyme. These compounds will, for the most part, have the following formula:

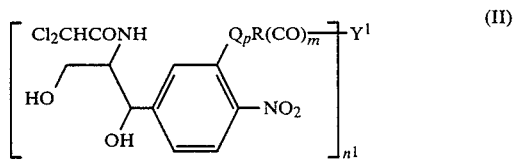

wherein Q, p, R, and m have been defined previously;

$Y^1$ is a poly(amino acid), functioning as an antigen or enzyme, of at least about 2,000 molecular weight, more usually of at least about 10,000 molecular weight and may be up to 10,000,000 molecular weight or greater, generally not exceeding about 600,000 molecular weight, more usually not exceeding about 300,000 molecular weight;

$n^1$ is at least 1, usually greater than 1, and generally not exceeding the molecular weight of $y^1$ divided by 1,000, more usually divided by 2,000 and will usually be at least the molecular weight of $y^1$ divided by 100,000, more usually the molecular weight of $y^1$ divided by 50,000; when $Y^1$ is functioning as an antigen, n is generally from about 1 to 100, more usually from about 5 to 80, and when $Y^1$ is functioning as an enzyme, n is usually from about 1 to 30, more usually 2 to 16.

With intermediate molecular weight antigens, whose having molecular weights in the range of about 20,000 to 600,000 the number of chloramphenicol groups which are bonded to the antigen will generally be from about 5 to 100, more usually from about 20 to 90, while with low molecular weight antigens, those from about 2,000 to 10,000 molecular weight, the number will generally be from about 1 to 20, more usually 2 to 10.

As indicated previously, of particular interest are compounds where the carbonyl funtionality, i.e., carbonyl group (other than keto) and the oxycarbonyl group or other substituted carbonyl derivative, is bonded to an amino group, which is part of a polypeptide or protein structure. One group of polypeptides and proteins is antigenic, so that by bonding the chloramphenicol analog of the present invention to the polypeptide or protein, the resulting material may be used to generate antibodies to chloramphenicol. A narrower class of proteins, which also can be used as antigens, but will not normally be used as such, are enzymes which are employed as the detector in an immunoassay system. As antigens, inactive enzymes can be used.

Polypeptides (referred to generally in the invention as poly(amino acid)) usually encompass from about 2 to 100 amino acid units (usually less than about 12,000 molecular weight). Larger polypeptides are arbitrarily called proteins. Proteins are usually composed of from 1 to 20 polypeptide chains called subunits, which are associated by covalent or noncovalent bonds. Subunits are normally of from about 100 to 300 or higher amino acid groups (or 10,000 to 35,000 or higher molecular weight). For the purposes of this invention, poly(amino acid) is intended to include individual polypeptide units and polypeptides which are subunits of proteins, whether composed solely of polypeptide units or polypeptide units in combination with other functional groups, such as porphyrins, as in hemoglobin or cytochrome oxidase.

As already indicated, the number of chloramphenicol groups will vary depending upon whether the poly(amino acid) is an enzyme or antigen. The maximum number of groups will be limited by the effect of substitution on solubility, activity, and the like. For the formation of antibodies, a sufficient number of chloramphenicol groups should be pesent, so as to provide a satisfactory harvest of antibodies to chloramphenicol. Otherwise, the proportion of antibodies to chloramphenicol as compared to antibodies to other compounds may be undesirably low. With monoclonal antibodies a reasonable number of hybridomas should result which secrete useful antibodies.

The first group of protein materials or polypeptides which will be considered are the antigenic polypeptides. These may be joined to the carbonyl functionality of the chloramphicol analog through an amino group. The product can be used for the formation of antibodies to chloramphenicol.

Various protein and polypeptide types may be employed as the antigenic material. These types include albumins, serum proteins, e.g. globulins, ocular lens proteins, lipoproteins, etc. Illustrative proteins include bovine serum albumin, keyhole limpet hemocyanin, egg albumin, bovine gamma-globulin, etc. Small neutral polypeptides which are immunogenic such as gramicidins may also be employed. Various synthetic polypeptides may be employed, such as polymers of lysine, glutamic acid, phenylalanine, tyrosine, etc., either by themselves or in combination. Of particular interest is polylysine or a combination of lysine and glutamic acid. Any synthetic polypeptide must contain a sufficient number of free amino groups as, for example, provided by lysine.

While the chloramphenicol analog may be bonded through the carbonyl functionality to hydroxyl or mercapto groups, which are present in the poly(amino acids), for the most part the bonding will be to amino groups.

Therefore, the compounds are described as amides, although esters and thioesters may also be present. The aldehyde derivative will be bonded solely to amino to form alkylamine groups through reductive amination.

Amino acids present in proteins which have free amino groups for bonding to the carbonyl-modified-chloramphenicol include lysine, N-terminal amino acids, etc. The hydroxy and mercaptan containing amino acids include serine, cysteine, tyrosine and threonine.

The second group of protein molecules are the detectors. These are the enzymes to which the carbonyl modified chloramphenicol may be conjugated.

Enzymes will normally be of molecular weights in the range of about 10,000 to 600,000, usually in the range of about 12,000 to 150,000, and more usually in the range of 12,000 to 80,000. Some enzymes will have a plurality of enzyme subunits. It is intended when speaking of enzyme molecular weights to refer to the entire enzyme. There will be on the average at least about one chloramphenicol per enzyme, when the labeling is not limited to a specific amino group, and rarely more than 30 chloramphenicols per enzyme, usually not more than 20 chloramphenicols per enzyme. For example, with lysozyme the average number of chloramphenicol groups would be in the range of about 2 to 5. For glucose-6-phosphate dehydrogenase the average number will be in the range of 2 to 20.

In accordance with the I.U.B. Classification, the enzymes of interest are: 1. Oxidoreductases, particularly Groups 1.1, and more particularly 1.1.1, and 1.11, more particularly, 1.11.1; and 3. Hydrolases, particularly 3.2, and more particularly 3.2.1. Various enzymes may be used such as peptidases, esterases, amidases, phosphorylases, carbohydrases, oxidases, e.g. dehydrogenase, reductases, and the like. Of particular interest are such enzymes as lysozyme, peroxidase, α-amylase, β-galactosidase, dehydrogenases, particularly malate dehydrogenase and glucose-6-phosphate dehydrogenase, alkaline phosphatase, β-glucuronidase, cellulase and phospholipase.

The substituted enzymes will for the most part have the following formula:

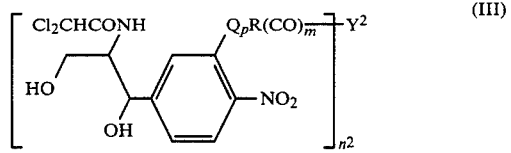

wherein Q, p, R, and m have been defined previously;

$Y^2$ is an enzyme substituted at other than the active site, and having at least 30 percent, preferably at least 50 percent, of its original activity prior to conjugation; and $n^2$ will usually be of from 1 to 30, more usually from 2 to 20, preferably 2 to 14, more preferably 2 to 12, but generally on the average equal to not more than about 60 percent of the total lysine groups available in the enzyme, although small enzymes such as lysozyme may have substantially all available lysine groups conjugated.

In forming the various amide products which find use in the subject invention, the carboxylic acid will normally be activated. This can be achieved in a number of ways. Two ways of particular interest are the reaction with a carbodiimide, usually a water soluble dialiphatic or dicycloaliphatic carbodiimide in an inert polar solvent, e.g. dimethylformamide, tetrahydrofuran, acetonitrile or hexamethylphosphoramide. The reaction is carried out by bringing the various reagents together under mild conditions and allowing sufficient time for the reaction to occur.

Another way is to use esters of the carboxy modified chloramphenicol which are operative in water for acylating amine functions. Illustrative of groups bonded to carboxy to provide activated esters which can be used in water are p-nitrophenyl and N-succinimidyl. For the aldehyde conjugation, a reductive amination is carried out in a polar, usually aqueous medium, employing sodium cyanoborohydride as the reducing agent.

The antibodies which are prepared in response to the conjugated antigens of this invention have strong specific binding to the parent drug, the conjugated antigen, the compound or derivative thereof used to conjugate to the antigen, and the chloramphenicol-labeled compounds, e.g., enzyme conjugates.

As previously indicated, the subject enzyme conjugates and antibodies find use in immunoassays. The enzyme conjugates of the subject invention are particularly useful in the method described in U.S. Pat. No. 3,817,837. In performing an effective immunoassay, there are many considerations. Since the aforementioned assay is spectrophotometric, one desires that there be a substantial change in signal with changing concentration of the analyte in the range of interest of the analyte. Thus, the antigenic conjugate must provide antibodies which when employed in combination with the enzyme conjugate, results in a sensitive response to variations in the chloramphenicol concentration.

In addition, there are a number of considerations about the antigen. Normally, one immunizes a number of animals with the antigen. Initial bleeds tend to have a low titer of low binding affinity, but within a relatively short time a plateau of titer and affinity is reached.

There is the further consideration of cross-reactivity. When determining a drug, one does not wish other drugs or naturally occurring compounds to affect the observed signal. Where other compounds are able to bind to various degrees to the antisera, the other compounds can have a substantial affect on the signal. This can be particularly true with metabolites, which are not in themselves active in the same manner as the drug precursor. Thus, in many situations, the antigen precursor must be designed to provide antibodies which will not significantly bind to metabolites of the analyte of interest.

The invention also includes compounds of the formula:

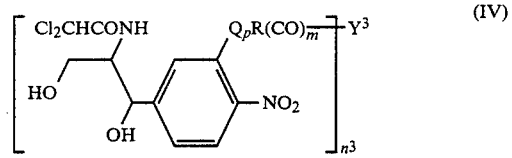

wherein:

Q and p have been defined previously;

R is a saturated aliphatic linking group of from 1 to 5 carbon atoms, usually 1 to 3 carbon atoms;

$Y^3$ is hydrogen, hydroxy, alkoxy of from 1 to 6 carbon atoms, or a group forming an activated ester capable of amide formation in an aqueous medium;

m is 1; and $n^3$ is 1.

The following compounds may be used to prepare the afore-described compounds of this invention:

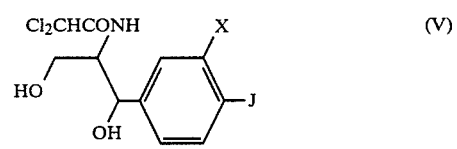

wherein:

X is halogen of atomic number 17 to 35; and

J is nitro or amino, including carbon-substituted amino.

In preparing the above compounds one may begin with chloramphenicol and convert the nitro group to an amino group as described in copending application U.S. Ser. No. 256,761, filed Apr. 23, 1981, by treating the chloramphenicol with a reducing agent such as sodium dithionite in an amount and under conditions sufficient to effect such conversion. The resultant product may be funtionalized by introduction of a halide atom such as bromine, into the aromatic ring using the procedure of Mitchell et al, *J. Org. Chem.*, 44:4733 (1979) wherein the above amino analog is treated with N-bromosuccinimide in N,N-dimethyl formamide in an amount and under conditions sufficient to achieve introduction of the halide atom. Following introduction of the halide atom the amino group is converted to a nitro group by Copper-Sandmeyer reaction according to Opgenorth et al., *Liebigs Ann. Chem.* 1333–1347 (1974). Because of the acid-base lability of chloramphenicol, reaction conditions for the above transformation should be mild. Accordingly, the bromoamino analog above is converted to its diazonium salt in a conventional manner and treated with excess copper-sodium nitrite under conditions sufficient to convert the amino group to a nitro group and give 3-bromochloramphenicol.

EXPERIMENTAL

The following examples are offered by way of illustration and not by way of limitation.

All temperatures not otherwise indicated are centigrade. Percents and parts not otherwise indicated are by weight, except for mixtures of liquids which are by volume. Abbreviations which are employed are as follows: THF—tetrahydrofuran; tlc—thin layer chromatography; h—hour; MeOH—methanol; DCC—dicyclohexyl carbodiimide; NHS—N-hydroxysuccinimide; HOAc—acetic acid; EDAC—ethyl dimethylaminopropyl carbodiimide; DMF—N,N-dimethylformamide; BSA—bovine serum albumin; BgG—bovine gamma globulin; G6PDH—glucose-6-phosphate dehydrogenase; NAD—nicotinamideadenine nucleotide.

EXAMPLE 1

Preparation of 1-(3'-bromo-4'-nitrophenyl)-2-dichloroacetamido-1,3-propanediol ("3-bromochloramphenicol")

A. Preparation of 1-(p-aminophenyl)-2-dichloroacetamido-1,3-propanediol. Chloramphenicol (Sigma, C-0378) (20 g, 62 mmol) and methanol (100 ml) were placed into a 1,000 ml round bottom flask. While nitrogen gas was bubbling through the solution, ice water (100 ml) was added. The reaction mixture precipitated and additional methanol (600 ml) was added. The temperature was kept between 0°–10° over the 30-minute reaction time.

To the above suspension were added solid sodium dithionite (32.9 g, 186 mmol) neat and sodium carbonate (150 ml, 5%) until the pH reached 7.0.

The reaction mixture was allowed to stir for 30 minutes, poured into ice water (250 ml), made basic (pH=8) with 5% $Na_2CO_3$, extracted with ethyl acetate (3×500 ml), washed (brine) (2×50 ml), dried over ($Na_2SO_4$), and concentrated in vacuo to give 3.53 g (19.4%) of a light yellow solid. Nmr ($CD_3OD$) δ 7.25–6.63 (q, 4), 6.28 (s, 1), 4.80 (d, 1, J=3 Hz), 4.05 (q, 1), 3.8–3.35 (m, 2), mp=124°–129° (decomposition), tlc-$R_f$=0.4, (eluting with $CH_2Cl_2$/MeOH/$NH_4OH$,84/12/4,v/v/v) $[\alpha]_D$= −2.86 ° (c=0.87 EtOH).

B. Preparation of 1-(3'-bromo-4'-aminophenyl)-2-dichloroacetamido-1,3-propanediol. To a solution of 1-(p-aminophenyl)-2-dichloroacetamido-1,3-propandiol (6.8 g) in 100 ml of N,N-dimethylformamide was added at room temperature under nitrogen, a solution of N-bromosuccinimide (4.1 g) in 100 ml of DMF for a period of 10 minutes. The reaction vessel was protected from being exposed to light throughout the reaction. The resulting dark red solution was allowed to stir at room temperature. After two hours, complete reaction was observed on a tlc plate (silica gel plate, 10% MeOH/$CH_2Cl_2$, product Rf 0.45, starting material Rf 0.30), and the resulting reaction product was then poured into 250 ml ice water and extracted with dichloromethane. The organic extracts were dried over $Na_2SO_4$ and evaporated to dryness in vacuo at 40° to yield a red oil.

The crude red oil, dissolved in MeOH/$CH_2Cl_2$, was added to flash chromatography silica gel (about 10 g) and the suspension was evaporated and dried in vacuo for 1½ hours, and the resulting powder was introduced onto a silica gel column (silica gel for flash chromatography, 80 g, Baker Chemical Co.) The column was then eluted with 1:1 ethyl acetate/hexane under a positive nitrogen pressure. The fractions corresponding to the reaction product were combined and evaporated to yield 7.9 g of product (91%). Anald. Calcd. for $C_{11}H_{13}N_2Cl_2BrO_3$: C, 35.56, H, 3.49; N, 7.53; Cl, 19.09; Br, 21.48; Found: C, 35.32; H, 3.74; N, 7.43; Cl, 19.38; Br, 21.29.

C. Preparation of diazonium salt of 1-(3'-bromo-4'-aminophenyl)-2-dichloroacetamido-1,3-propandiol.

To a solution, under nitrogen at 0°, of 1-(4'-aminophenyl-3'-bromo)-2-chloroacetamido-1,3-propandiol from above (4.66 g) in ethanol (24 ml) was added fluoroboric acid (Eastman Chemical Co., 5 ml, 49% in water) followed by a solution of sodium nitrite (1 g) in 1.7 ml of water. The resulting red solution was allowed to stir at room temperature under nitrogen. After one hour, complete reaction was observed on tlc (silica gel, 10% MeOH/$CH_2Cl_2$, complete disappearance of starting material).

The resulting suspension was allowed to evaporate to dryness using an evaporator and the orange solid was triturated using about 50 ml of ether and then evaporated to dryness. The solid thus obtained was dried at room temperature under vacuum overnight and used directly without further purification.

D. The crude diazonium salt from above, dissolved in 160 ml of water, was divided into four portions and was then kept frozen using dry ice bath. Each portion of the diazonium salt was defrosted before use (at 25°) and then added through a dropping funnel for a period of ½ hour into a suspension of copper (14.4 g), sodium nitrite (110 g) in 400 ml of water. The addition of reagents took about 2 hours totally, and the resulting greenish-brown suspension was allowed to stir at room temperature for two additional hours. Complete reaction was observed on tlc (silica gel, 10% MeOH/$CH_2Cl_2$ starting material Rf 0.43, product Rf 0.48).

The suspension was filtered and the inorganic precipitates were collected and washed with ethyl acetate. The entire filtrate was then extracted with ethyl acetate and the organic layers were combined and dried over sodium sulfate. Evaporation of solvents gave a brown residue which was purified using flash chromatography. Purification: The crude product was dissolved in ethyl acetate to which was added about 6 g of silica gel (Baker silica gel for flash chromatography). The resulting suspension was evaporated to dryness and was placed onto a column containing about 60 g of silica gel (Baker Chemical Co. silica gel for flash chromatography) and eluted with 1:1 ethyl acetate/hexane. The fractions were collected and pure samples (3.0 g) of "3-bromochloramphenicol" were obtained. m.p. 119°–124°; m/e $[M+NH_4]^+ 420$; Calcd. for $C_{11}H_{11}N_2O_5BrCl_2$: C, 32.84; H, 2.74; N, 6.97; Br, 19.88; Cl, 17.66; Found: C, 33.00; H, 2.89; N, 6.78; Br, 19.91; Cl, 17.88.

EXAMPLE II

Preparation of 1-(3'-Carboxymethylenethio-4'-nitrophenyl)-2-dichloroacetamido-1,3-propanediol ("chloramphenicol mercaptoacetic acid")

Mercaptoacetic acid (400 μl) was added at 5° under nitrogen to a suspension of sodium hydride (554 mg, 50% in oil) in DMF (11.6 ml) for a period of 10 minutes. After 15 minutes, the resulting white suspension was then added to a solution of 1-(3'-bromo-4'-nitrophenyl)-2-dichloroacetamido-1,3-propanediol from above (2.3 g, 5.77 mmole) in DMF (15 ml). After 90 hours at 5°, both reaction products and starting material were shown on tlc (silica gel plate, 0.1:1:9 acetic acid/MeOH/$CH_2Cl_2$.

The dark brown reaction product was evaporated to dryness under reduced pressure (at 40°), and the residue was then suspended in a small amount of MeOH/$H_2O$ and acetic acid was added until pH 5. The brown solution was then purified on eight thick layer plates (1:20:79 acetic acid/MeOH/$CH_2Cl_2$). The bands were recovered by eluting with 1:2 MeOH:$CH_2Cl_2$, and 660 mg yellow solid of "chloramphenicol mercaptoacetic acid".

The yellow solid of "chloramphenicol mercaptoacetic acid" was further purified on silanized silica gel column as follows: "Chloramphenicol mercaptoacetic acid" in 50% aqueous methanol (2 ml) was mixed with silica gel (silanized, pre-washed, 2 g) and the resulting suspension was evaporated to dryness and then under vacuum for 3 h. at room temperature. The yellow residue was then applied to a column containing silanized silica gel and then eluted with 50 ml of dichloromethane, 2% MeOH/$CH_2Cl_2$, 6% MeOH/$CH_2Cl_2$, respectively; and then 15% MeOH/$CH_2Cl_2$ until the desired product was eluted out. The fractions which contained the desired product were combined and evaporated to yield 80 mg of orange-brown product of "chloramphenicol mercaptoacetic acid". $[\alpha]_D = -8.2°$, C=5 mg/ml.

EXAMPLE III

Preparation of the 1-(3'-carboxylmethylenethio-4'-nitrophenyl)-2-dichloroacetamido-1,3-propanediol conjugate of BgG A. Preparation of the N-Hydroxysuccinimide Ester of "Chloramphenicol Mercaptoacetic Acid."

To a solution of chloramphenicol mercaptoacetic acid from Example II (18 mg, 0.043 mmole) dissolved in 0.5 ml of DMF was added powdered EDCI (9.2 mg, 0.048 mmole) and NHS (6 mg, 0.052 mmole) at 5° under nitrogen. After 18 hours, reaction was found to be completed using tlc (silica gel plate, 10% MeOH/$CH_2Cl_2$, NHS ester of chloramphenicol mercaptoacetic acid, Rf 0.26, starting material, Rf 0.08).

B. Conjugation of Chloramphenicol Mercaptoacetic Acid to BgG

The NHS ester of chloramphenicol mercaptoacetic acid (prepared from 35 mg [0.048 mmole] of acid, EDCI [16.38 mg], and NHS [12 mg] in 0.9 ml of DMF according to the procedure of Example IIIA above was added to a solution of bovine gamma globulin (300 mg) in 200 ml of phosphate buffer (20 ml) at 0° with the constant adjustment of pH to 8.5 for a period of 1.5 h. The resulting yellow solution was then allowed to stir overnight at 5°. The solution was then passed through Sephadex G-50 (eluted with phosphate buffer, pH 8.5, 0.05M). The protein fractions were combined and dialyzed against $4 \times 4$ l.$NH_4OH/H_2O$ (pH 7.5) at 5°. The conjugate was then lyophilized to yield a protein conjugate (310 mg) of hapten number 33.

EXAMPLE IV

Preparation of the 1-(3'-carboxylmethylmethio-4'-nitrophenyl-2-dichloroacetamido-1,3-propanediol conjutate of BSA The NHS ester of chloramphenicol mercaptoacetic acid (prepared from 30 mg of acid as in Example IIIA above in DMF was added at 0° to a solution of BSA (100 mg) in 7.5 ml of phosphate buffer (pH 8.5, 0.05M) and 0.8 ml of DMF, for a period of 40 minutes with the constant adjustment of pH to 8.5. The resulting mixture was then allowed to stir at 5° for 72 hours.

The resulting conjugate was centrifuged at 0° at 5K for 10 minutes and the supernatant was then passed through Sephadex G-50 and eluted with phosphate buffer (pH 8.5, 0.05M). The conjugate was then dialyzed at pH 7 ($NH_4OH/H_2O$, $4 \times 4$ liter) for 2 days and then lyophilized to yield 98 mg protein of hapten number 16.

EXAMPLE V

Preparation of the 1-(3'-carboxymethylenethio-4'-nitrophenyl)-2-dichloroacetamido-1,3-propanediol conjugate of G6PDH 1-(3'-Carboxymethylenethio-4'-nitrophenyl)-2-dichloroacetamido-1,3-propanediol prepared as in Example II (5 mg), was weighed under dry conditions into a dry pearshaped flask. Then, 120 μl of DMF was added to the flask to solubilize the contents. Next, 2 mg of NHS and 2.6 mg of EDAC were added to the flask after flushing with nitrogen. After further flushing with nitrogen the flask and its content were held for 20 h. at 5°. Twelve μl of this solution was slowly added at 4° to a solution containing 3.8 mg of G6PDH (Beckman Co., Fullerton, CA) and 60 mg glucose-6-phosphate disodium salt [G6P(Na$_2$), Sigma Co.] in 0.5 ml of 0.055M Tris buffer, pH 8. When the enzyme activity had decreased to 65–75% of its original activity, the reaction mixture was chromatographed on a $19 \times 1.9$ cm column of Sephadex G-50 (Pharmacia, Piscataway, N.G.) an eluted with 0.055M Tris buffer, pH 8, containing 0.05% sodium azide and 0.005% thimerosal at a flow rate of 3 mls/min. Fractions of about 1 ml were collected and those fractions containing high enzyme activity (usually fractions 17 to 24, total volume=7 ml) were pooled as the G6PDH conjugate of 1-(3'-carboxymethylenethio-4'-nitrophenyl)-2-dichloroacetamido-1,3-propanediol.

EXAMPLE VI

The compositions prepared above were used in assays for chloramphenicol. The assay employed the following reagents:

TABLE I

| | |
|---|---|
| Buffer: | 0.055 M Tris-HCl, pH 8.1 (RT), 0.05% NaN$_3$, 0.005% Thimerosal |
| Assay Buffer: | Buffer, 0.5% NaCl, 0.01% (v/v) Triton X-100, pH 8.1 (RT) |
| Reagent A: | Buffer, 1.0% RSA, 0.066 M G6P (Na$_2$), 0.04 M, NAD, pH 5 (RT) antichloramphenicol optimized for response |
| Reagent B: | Buffer, 0.9% NaCl, 1.0% RSA, 0.032 M G6P (Na$_2$), pH 6.2, sufficient enzyme to give a maximum rate of 700 $\Delta$OD. |

Protocol: 50 $\mu$l of the sample is drawn up into a diluter and dispensed with 250 $\mu$l of the assay buffer into a 1 ml Croan cup. A 50 $\mu$l aliquot of the diluted sample is drawn up and dispensed with 250 $\mu$l portion of assay buffer into a second Croan cup. Into the second Croan cup is introduced 50 $\mu$l of the antibody reagent with 250 $\mu$l of the assay buffer, followed by the addition of 50 $\mu$l of the enzyme reagent and 250 $\mu$l of the assay buffer. Immediately after the enzyme addition, the entire sample is aspirated into the flow cell. After 15 sec., a first reading is taken, followed by a second reading after a 30-sec. interval. The results are reported as the difference in absorbence $\times$ 2.667.

Two sheep were immunized with the antigen according to Example III. The antisera (4580 and 4583) produced at the C bleed were tested for optimal assay response (O.D.) and for effective titer. The opimal assay response is the optimal separation in O.D. units between 2.5 $\mu$g/ml or 40 $\mu$g/ml chloramphenicol calibrators. This response shows the best range of the standard curve obtainable in accordance with the above described protocol. The larger optimal assay response, the better the precision and accuracy. Effective titer is the amount of antiserum required per assay to give the optimal assay response. The higher the titer, the lower the required quantity of antiserum, the less extensive the assay production costs are the less extraneous material introduced into the assay medium.

The above procedure was repeated using the antigen according to Example IV and one sheep to give antiserum 4612.

The following table reports the results of the three antisera.

TABLE II

| Antiserum | Optimal Assay Response O.D. neg→2.5 | Optimal Assay Response O.D. neg→40 | Effective Titer ($\mu$l) |
|---|---|---|---|
| 4580 | 70 | 180 | 1.2 |
| 4583 | 60 | 160 | 1.6 |
| 4612 | 70 | 160 | 2.5 |

The percent deactivation of the enzyme-conjugate was 65–75% depending on percent inhibition endpoint.

Cross reactivity was determined against metabolites of chloramphenicol, none of which are active, as well as other drugs. Of the five known metabolites of chloramphenicol, 1-p-nitrophenyl-2-amino-1,3-propanediol; 1-p-aminophenyl-2-dihydroxyacetamido-1,3-propanediol; 1-p-aminophenyl-2-amino-1,3-propanediol, 1-p-nitrophenyl-2-dihydroxyacetamido-1,3-propanediol, and 1-p-acetamidophenyl-2-dichloroacetamido-1,3-propanediol, none of the metabolites showed significant activity, which is defined as the concentration of a compound which, when spiked into a 15 $\mu$g/ml control, will give a response in the assay equal to the response of 130% (i.e. 19.5 $\mu$g/ml) of the concentration of the 15 $\mu$g/ml control, the cross reactivity concentration for the second compound was 2 $\mu$g/ml. Only the chloramphenicol succinate salt showed some cross reactivity. Based on an independent study of a comparison between the above assay and HPLC with patient samples, which showed good correlation statistics between the two techniques, the effect of the cross reactivity on the subject assay to correctly quantitate chloramphenicol is believed to be minimal.

The compositions of the subject invention are reagents which provide a sensitive accurate assay for chloramphenicol, distinguishing chloramphenicol from closely related metabolites. The antigenic conjugate provides for the efficient production of antibodies having high affinity and high titer for chloramphenicol. The combination of the antibodies and enzyme conjugates result in an accurate rapid assay for chloramphenicol in serum.

Although the foregoing invention has been described in some detail by way of illustration and example for purposes of clarity of understanding, it will be obvious that certain changes and modifications may be practiced within the scope of the appended claims.

What is claimed is:

1. A compound of the formula:

$$\left[ \begin{array}{c} Cl_2CHCONH \\ HO \end{array} \diagdown \diagup \underset{OH}{\diagdown} \diagup \bigcirc \underset{NO_2}{\overset{Q_pR(CO)_m}{\diagup}} \right]_n Z$$

wherein:
Q is chalcogen of atomic number 8 to 16 or nitrogen;
p is 0 or 1;
R is a linking group of at least 1 carbon atom and not more than 12 atoms other than hydrogen;
Z is hydrogen, hydroxy, alkoxy of from 1 to 6 carbon atoms, a group forming an activated ester capable of amide formation in an aqueous medium, or a poly(amino acid) which is antigenic or an enzyme;
m is 0 or 1 when Z is a poly(amino acid) and is otherwise 1; and
n is 1 when Z is other than a poly(amino acid) and is otherwise a number between one and the molecular weight of Z divided by 1000.

2. The compound of claim 1 wherein R is a polymethylene of from 1 to 5 carbon atoms.

3. The compound of claim 2 wherein Q is sulfur, p is 1, R is one carbon atom, and m is 1.

4. A compound of the formula:

$$\left[ \begin{array}{c} Cl_2CHCONH \\ HO \end{array} \diagdown \diagup \underset{OH}{\diagdown} \diagup \bigcirc \underset{NO_2}{\overset{Q_pR(CO)_m}{\diagup}} \right]_{n1} Y^1 \quad (II)$$

wherein:

Q is chalcogen of atomic number 8 to 16 or nitrogen, p is 0 or 1;
R is a saturated aliphatic linking group of from 1 to 6 carbon atoms;
$Y^1$ is a poly(amino acid);
m is 0 or 1; and
$n^1$ is a number divided between one and the molecular weight of $Y^1$ divided by 2000.

5. The compound of claim 4 wherein Q is sulfur, p is 1, R is one carbon atom, and m is 1.

6. The compound of claim 4 wherein $Y^1$ is an antigen.

7. The compound of claim 4 wherein $Y^1$ is serum albumin.

8. The compound of claim 4 wherein $Y^1$ is gamma globulin.

9. Antibodies prepared in response to the compound of claim 6.

10. The compound of claim 4 wherein $Y^1$ is an enzyme.

11. The compound of claim 10 wherein said enzyme is glucose-6-phosphate dehydrogenase.

12. A compound of the formula:

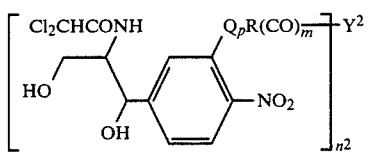

wherein:
Q is chalcogen of atomic number 8 to 16 or nitrogen; p is 0 or 1;
R is a linking group of from 1 to 12 atoms other than hydrogen;
$Y^2$ is an enzyme substituted at other than the active site, and having at least 30 percent of its original activity prior to conjugation;
m is 0 or 1; and
$n^2$ is 1 to 30.

13. A compound of the formula:

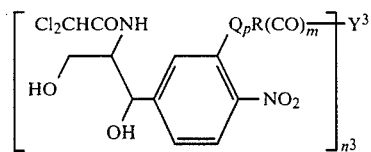

wherein:
Q is chalcogen of atomic number 8 to 16 or nitrogen; p is 0 or 1;
R is a saturated aliphatic linking group of from 1 to 8 carbon atoms;
$Y^3$ is hydrogen, hydroxy, alkoxy of from 1 to 6 carbon atoms, or a group forming an activated ester capable of amide formation in an aqueous medium;
m is 1; and
$n^3$ is 1.

14. The compound of claim 13 wherein Q is sulfur, p is 1, R is methylene, $n^3$ is 1, and $Y^3$ is hydroxy.

15. A method for preparing a compound of the formula

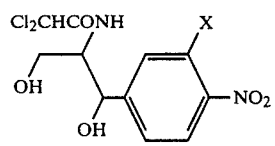

wherein X is halogen, which compound is employed as a precursor in the preparation of the compound of claim 1, which method comprises:
(a) converting the nitro group of chloramphenicol to an amino group,
(b) introducing a halogen atom into the aromatic nucleus of the compound of Step (a), and
(c) converting the amino group introduced in Step (a) to a nitro group.

* * * * *